(12) United States Patent
Isola et al.

(10) Patent No.: US 10,765,891 B2
(45) Date of Patent: Sep. 8, 2020

(54) EVALUATION OF DOSE ACCURACY OF RADIATION THERAPY TREATMENT PLANS

(71) Applicant: KONINKLIJKE PHILIPS N.V., Eindhoven (NL)

(72) Inventors: Alfonso Agatino Isola, Eindhoven (NL); Rolf Jürgen Weese, Norderstedt (DE); Christoph Neukirchen, Aachen (DE); Steffen Renisch, Hamburg (DE); Hrishikesh Narayanrao Deshpande, Hamburg (DE); Heinrich Schulz, Hamburg (DE); Sven Kabus, Hamburg (DE); Stéphane Allaire, Nanterre (FR); Maria Luiza Bondar, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 39 days.

(21) Appl. No.: 16/172,958

(22) Filed: Oct. 29, 2018

(65) Prior Publication Data
US 2019/0143147 A1 May 16, 2019

(30) Foreign Application Priority Data
Nov. 15, 2017 (EP) .................................... 17306584

(51) Int. Cl.
*A61N 5/10* (2006.01)
*G16H 20/40* (2018.01)

(52) U.S. Cl.
CPC ............ *A61N 5/1075* (2013.01); *A61N 5/103* (2013.01); *A61N 5/1031* (2013.01);
(Continued)

(58) Field of Classification Search
CPC ............ A61N 2005/1041; A61N 5/103; A61N 2005/1074; A61N 5/1031
See application file for complete search history.

(56) References Cited

U.S. PATENT DOCUMENTS

| 6,222,544 B1 | 4/2001 | Tarr |
| 2011/0153547 A1 | 6/2011 | McNutt |

(Continued)

OTHER PUBLICATIONS

Masi et al., "Impact of plan parameters on the dosimetric accuracy of volumetric modulated arc therapy", Med. Phys. 40 (7), pp. 071718.1-071718.11, 2013.
(Continued)

*Primary Examiner* — David P Porta
*Assistant Examiner* — Fani Boosalis (57) ABSTRACT

The invention relates to a system and a method for evaluating a treatment plan for an external radiation therapy treatment, the treatment plan comprising parameters for controlling an external radiation therapy apparatus during the treatment. The system comprises a database storing historic treatment plans and storing for each historic treatment plan a quality parameter indicative of whether a deviation between a planned dose distribution and a measured dose distribution resulting from an execution of the treatment plan is within an acceptable limit. An evaluation unit determines a threshold value for each of a plurality of treatment plan metrics based on the historic treatment plans and the associated quality parameters. Further, the evaluation unit calculates a value of each of the metrics for the treatment plan and compares the value of each of the metrics with the threshold value determined for the respective metric.

20 Claims, 3 Drawing Sheets

(52) U.S. Cl.
CPC ........... *A61N 5/1077* (2013.01); *G16H 20/40* (2018.01); *A61N 2005/1041* (2013.01); *A61N 2005/1074* (2013.01)

(56) References Cited

U.S. PATENT DOCUMENTS

| | | | |
|---|---|---|---|
| 2014/0304206 A1 | 10/2014 | Lee | |
| 2016/0140300 A1* | 5/2016 | Purdie | G16H 20/10 705/2 |
| 2017/0072221 A1 | 3/2017 | Nord | |
| 2017/0259082 A1 | 9/2017 | Bzdusek | |

OTHER PUBLICATIONS

Younge et al., "Predicting deliverability of volumetric-modulated arc therapy (VMAT) plans using aperture complexity analysis", Journal of Applied Clinical Medical Physics, vol. 17, No. 4, pp. 124-131, 2016.

Wendling et al., "A fast algorithm for gamma evaluation in 3D", Med. Phys. 34(5):1647-54, 2007.

Park et al. "The effect of MLC speed and acceleration on the plan delivery accuracy of VMAT", Br J Radiol 2015; 88:20140698.

Giorgia et al., "What is an acceptably smoothed fluence? Dosimetric and delivery considerations for dynamic sliding window IMRT", Radiation Oncology 2007, 2:42.

Crowe et al., "Treatment plan complexity metrics for predicting IMRT pre-treatment quality assurance results", Australas Phys Eng Sci Med (2014) 37:475-482.

Crowe et al., "Examination of the properties of IMRT and VMAT beams and evaluation against pretreatment quality assurance results", Phys. Med. Biol. 60 (2015) 2587-2601.

Huang et al., "Impact of small MU/segment and dose rate on delivery accuracy of volumetric-modulated arc therapy (VMAT)", Journal of Applied Clinical Medical Physics, vol. 17, No. 3, pp. 203-210, 2016.

McNiven et al., "A new metric for assessing IMRT modulation complexity and plan deliverability", Med. Phys. 37, 505-515 (2010).

Mitchell, "Evaluating Pre-Treatment IMRT & VMAT QA Techniques Using Receiver Operating Characteristic (ROC) Analysis" 2013.

* cited by examiner

EVALUATION OF DOSE ACCURACY OF RADIATION THERAPY TREATMENT PLANS

CROSS REFERENCE TO RELATED APPLICATIONS

This application claims the benefit of European Patent Application Number 17306584.8 filed Nov. 15, 2017. This application is hereby incorporated by reference herein.

FIELD OF THE INVENTION

The invention relates to the evaluation of treatment plans for a radiation therapy treatment. More specifically, the invention is related to a system and a method for evaluating a treatment plan for an external radiation therapy treatment of a patient.

BACKGROUND OF THE INVENTION

In external beam radiation therapy, ionizing radiation is applied to target structures, such as tumors, within patients' bodies in order to control growth of or kill cancer cells. In advanced types of radiation therapy, such as volumetric modulated arc therapy (VMAT) and intensity-modulated radiation therapy (IMRT), precise doses of radiation are applied to regions of the patient's body to deliver a sufficiently high radiation dose to the target structure and to spare sensitive structures, which are also referred to as organs at risk (OARs), as far as possible.

In order to achieve this, radiation therapy apparatuses used in these types of radiation therapy comprise a collimator in addition to the radiation source and the collimator shapes the radiation beam generated by the radiation source such that a prescribed radiation dose is delivered to the target structure while the radiation dose delivered to the OARs is as low as possible. The collimator is usually configured as a multileaf collimator (MLC) comprising a plurality of leaves which can be independently moved in and out of the radiation beam to thereby shape the cross section of the beam.

The control parameters for controlling the radiation therapy apparatuses and the included radiation source and the collimator during the delivery of the treatment are provided in a treatment plan which is determined in a planning system. In the planning system, the treatment plan may be determined using an inverse planning procedure. In such a procedure, dose goals are specified for the target structure and the OARs in accordance with a medical prescription. Then, an optimization process is carried out to find optimized treatment parameters such that the radiation dose distribution corresponding to the treatment plan—which is also referred to as planned dose distribution herein—fulfills the dose goals.

In the planning procedure, the radiation dose distribution is particularly estimated on the basis of a model for simulating the operation of the radiation therapy apparatus and the included particle source and the collimator. However, the mechanical characteristics and limitations of radiation therapy apparatuses are quite complex so that an accurate modeling is often not possible. In particular, the collimator is difficult to model, e.g. in view of its limitations with respect to leaf travel and interleaf leakage. In VMAT, further inaccuracies result from the fact that radiation is continuously delivered during the treatment whereas the planning process is carried out on the basis of discretized positions of the radiation source.

As a consequence of these inaccuracies, the actual dose distribution resulting from an execution of a treatment plan by means of the radiation therapy apparatus may deviate significantly from the planned dose distribution so that the treatment goals are not fulfilled.

In view of these potential errors, treatment plans usually undergo a quality assurance (QA) test prior to the delivery of the treatment in order to assess the dose accuracy of the treatment plan. In the QA test, the treatment plans are executed by means of the radiation therapy treatment system using a phantom which is configured to measure the delivered dose distribution. When this test reveals an unacceptable deviation between the actually delivered dose distribution and the planned dose distribution, the treatment plan is not used for delivering the treatment to the patients and a revised treatment plan is determined for the treatment of the patient, which then has to undergo a further QA test.

The QA testing of treatment plans is time-consuming and expensive. Therefore, it is desirable to recognize as many unacceptable treatment plans as possible, already before the execution of the QA test. For these treatment plans, the execution of the actual QA test can be dispensed with so that the number of failed QA test can be reduced.

In this respect, systems are known which evaluate treatment plans by determining a particular metric for the treatment plans and by comparing the determined values of the metric with a threshold value in order to predict whether a treatment plan is acceptable, i.e. whether it passes the QA test. For instance, the publication L. Masi et al., "Impact of plan parameters on the dosimetric accuracy of volumetric modulated arc therapy", Med. Phys. 40 (7), pp. 071718.1-11, 2013, suggests calculating an average leaf travel for VMAT treatment plans as a metric and to compare the average leaf travels of the treatment plans with a threshold of 450 mm in order to validate the treatment plans. The publication K. C. Younge et al., "Predicting deliverability of volumetric-modulated arc therapy (VMAT) plans using aperture complexity analysis", Journal of Applied Clinical Medical Physics, Vol. 17, No. 4, pp. 124-131, 2016, proposes calculating a special complexity metric which is compared with a particular threshold ($0.18$ $mm^{-1}$) in order to predict whether a treatment plan will pass the QA test.

However, it has been found that the metrics used in these systems are relatively unreliable so that a relatively large number of treatment plan which were successfully validated using these metrics do not pass the QA test. Thus, a relatively large number of failing QA tests still has to be performed in the known systems.

SUMMARY OF THE INVENTION

It is an object of the invention to allow for a more reliable validation of treatment plans for an external beam radiation therapy treatment so that the number of failing QA tests can be further reduced.

In accordance with one aspect, the invention suggest a system for evaluating a treatment plan for an external radiation therapy treatment of a patient delivered using an external beam radiation therapy apparatus, the treatment plan comprising parameters for controlling the external beam radiation therapy apparatus during the treatment. The system comprising:

a database storing a plurality of historic treatment plans and storing for each historic treatment plan a quality parameter indicative of whether a deviation between a planned dose distribution corresponding to the respective treatment plan and a measured dose distribution resulting from an execution of the treatment plan is within an acceptable limit, and an evaluation unit configured to determine a threshold value for each of a plurality of treatment plan metrics on the basis of the historic treatment plans and the associated quality parameters, and further configured to calculate a value of each of the metrics for the treatment plan and to the compare the value of each of the metrics with the threshold value determined for the respective metric and to provide the result of the calculation and/or the comparison for a validation of the treatment plan.

Since the system evaluates a plurality of different treatment plan metrics rather than a single metric, the treatment plan can be evaluated more reliably with respect to its dose accuracy. In particular, it is possible to more reliably predict whether the treatment plan will successfully pass the QA test so that a larger number of failed QA tests can be avoided. In this respect, the system may be configured to carry out a QA test for the treatment plan if the treatment is accepted as the result of its validation.

Moreover, the system is enabled to determine the threshold values on the basis of the historic treatment plans and the related quality parameters stored in the database so that it is possible to automatically determine reliable threshold values (in case a sufficiently large number of historic treatment plans is available in the database).

The database may store treatment plans and related quality parameters indicative of whether the deviation between a planned dose distribution and a measured dose distribution resulting from an execution of the treatment plan in the external beam radiation therapy apparatus is within an acceptable limit. Thus, it is possible to take the characteristics of this apparatus into consideration. However, the database may likewise store historic treatment plans which have been tested with respect to their dose accuracy in other apparatuses.

In one embodiment of the invention, the evaluation unit is configured to determine the threshold values for the treatment plan metrics on the basis of a statistical analysis of the quality parameters associated with the treatment plans stored in the database. The statistical analysis carried out for determining a threshold value for a particular treatment plan metric may particularly comprise a correlation analysis between the values of the treatment plan metric for the historic treatment plans and the related quality parameters.

In a further embodiment of the invention, the quality parameter associated with a treatment plan comprises an indication of a result of a QA test of the treatment plan and/or gamma indices determined for the treatment plan. It has been found that these quality parameters allow for an especially reliably determination of threshold values for the treatment plan metrics.

Moreover, the reliability of the threshold values determined on the basis of a statistical evaluation of the historic treatment plans and the related quality parameters stored in the database generally increases with the number of historic treatment plans included in the database. Therefore, one embodiment of the invention comprises that the database can be updated to store further treatment plans and associated quality parameters and that the evaluation unit is configured to adapt the determined threshold values to the further treatment plans upon an update of the database. Hereby, it is possible to improve the threshold values determined in the evaluation unit over time. It can particularly be provided that each treatment plan for which a QA test is newly performed is included in the database together with the related quality parameters.

In a further embodiment of the invention, the evaluation unit is configured to receive a threshold value input by a user of the system for at least one of the treatment plan metrics and to compare the calculated value for the respective treatment plan metric with said threshold value instead of the threshold value determined on the basis of the historic treatment plans and the associated quality parameters. Moreover, an automatic determination of threshold values for one or more further treatment plan metrics may be dispensed with. Therefore, one embodiment of the invention includes that the evaluation unit is configured to receive a threshold value input by a user of the system for at least one further treatment plan metric, to calculate a value of the further metric for the treatment plan and to compare the calculated value with said threshold value and/or to provide the result of the calculation and/or the comparison for a validation of the treatment plan.

In the aforementioned embodiments, it is possible for the user to manually specify threshold values which take precedence over automatically generated threshold values or to manually specify threshold values for one or more treatment plan metrics without a preceding automatic determination. These options may particularly be used in case the database does not (yet) contain a sufficiently large number of treatment plans and associated quality parameters to allow for an automatic determination of reliable threshold values. In this case, more reliable threshold values can be specified by the user on the basis of is expert knowledge and past experience.

In a further embodiment of the invention, the evaluation unit is further configured to compare the calculated value of each the metrics with an associated further flexibility threshold, where the value of the flexibility threshold does not comply with the threshold values determined for the metric. In particular, the flexibility threshold may be selected in such a manner that a value which does not comply with the threshold value but is compliant with the flexibility threshold might be regarded as being acceptable, at least under certain circumstance, e.g. if the values of all or most of the other treatment plan metrics are compliant with the related threshold values.

Furthermore, the evaluation unit is preferably configured to present the calculated values of the metrics to a user of the system in a graphical user interface in order to allow for a validation of the treatment plan by the user. Hereby, the system facilitates the validation of the treatment plan by a user on the basis of the plurality of different treatment plan metrics. Moreover, the graphical user interface including values for all treatment plan metrics stored in the system allows for standardizing the review of treatment plans in a clinical environment.

In order to further assist the user in evaluating the treatment plan, the evaluation unit may also be configured to highlight the calculated values in the graphical user interface based on their compliance with the threshold value determined for the respective metric and/or with the associated flexibility threshold. Thus, it is possible for the user to quickly identify the values of the metrics which are not compliant with the threshold value and/or the flexibility threshold.

In particular, the values which are not compliant with both the threshold value and the flexibility threshold may be highlighted in one predefined manner, which may include a highlighting in a particular color, such as red. Moreover, values which are not compliant with the threshold value but with the flexibility threshold may be highlighted in another manner, which may include a highlighting using another color, such as yellow.

In a further embodiment of the invention, the evaluation unit is configured to present the calculated values of the metrics in the graphical user interface only in case the calculated value of at least one metric is not compliant with its associated threshold value. In a related embodiment, the evaluation unit is configured to automatically accept the treatment plan if the calculated values of all metrics are compliant with their associated thresholds. In these embodiments, a semi-automatic evaluation of the treatment plan is made possible in which the user of the system is only asked to manually review the treatment plan in case one value of a treatment plan metric is not compliant with the related threshold value. Hereby, the efficiency of the review process can be improved.

In accordance with a further aspect, the invention suggests a method for evaluating a treatment plan for an external radiation therapy treatment of a patient delivered using an external beam radiation therapy apparatus, the treatment plan comprising parameters for controlling the external beam radiation therapy apparatus during the treatment. The method comprises:

storing a plurality of historic treatment plans in a database and storing for each historic treatment plan a quality parameter indicative of whether a deviation between a planned dose distribution corresponding to the respective treatment plan and a measured dose distribution resulting from an execution of the treatment plan in the external beam radiation therapy apparatus is within an acceptable limit, determining a threshold value for each of a plurality of treatment plan metrics on the basis of the historic treatment plans and the associated quality parameters, calculating a value of each of the metrics for the treatment plan, comparing the value of each of the metrics with the threshold value determined for the respective metric, and providing the result of the calculation and/or the comparison for a validation of the treatment plan.

In accordance with a further aspect, the invention suggests a computer program comprising program code for instructing a computer device to perform the method when the program code is executed in the computer device.

It shall be understood that the system of a representative embodiment, the method of another representative embodiment, and the computer program of another representative embodiment have similar and/or identical additional embodiments.

It shall be understood that an embodiment of the present invention can also be any combination of additional embodiments.

These and other aspects of the invention will be apparent from and elucidated with reference to the embodiments described hereinafter.

DETAILED DESCRIPTION OF EMBODIMENTS

Figure 1:
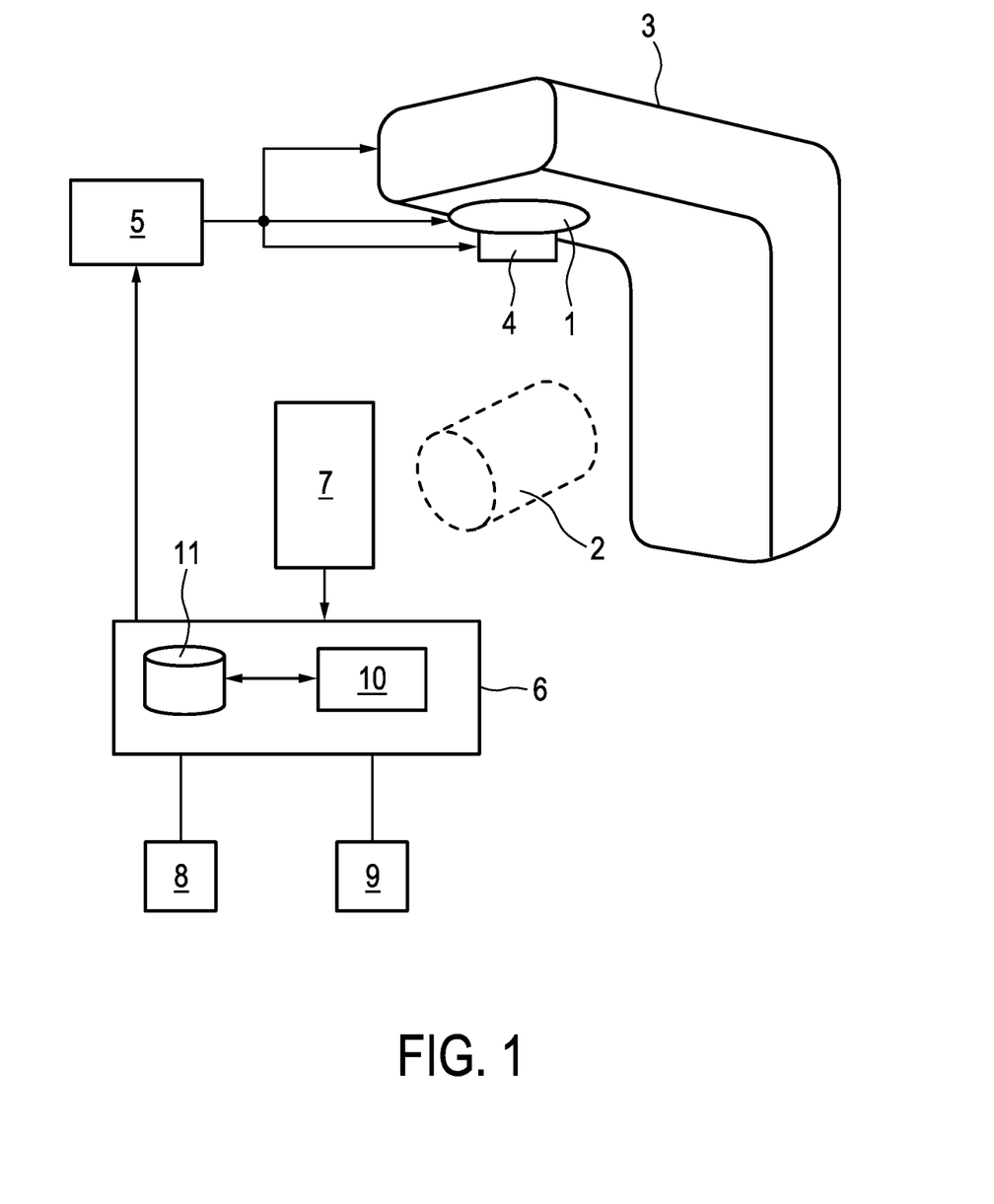
FIG. 1 schematically and exemplarily illustrates components of a system for planning and delivering external beam radiation therapy treatments, FIG. 2 schematically and exemplarily illustrates a graphical user interface for presenting values of treatment plan metrics to a user of the system for review, and FIG. 3 schematically and exemplarily shows steps of one embodiment of method for evaluating a treatment plan in the system.

FIG. 1 schematically and exemplarily illustrates an embodiment of a system for planning and delivering external beam radiation therapy treatments to target structures in patient bodies. The target structures may particularly be tumors which are irradiated with ionizing radiation in order kill cancer cells.

The radiation therapy delivery system comprises a radiation source 1, which can be operated to emit ionizing radiation into a treatment zone 2. In the treatment zone 2, the patient body is positioned on a suitable support, such as a patient table (not shown in the figures). The relative position and orientation of the radiation source 1 with respect to the relevant body region including the target structure can be varied over a certain range of positions and orientations. For this purpose, the radiation source 1 may be mounted on gantry 3 which can be rotated around the treatment zone 2 within a certain angular range. In addition, the gantry 3 and the patient support may be movable relative to each other with respect to various degrees of freedom in order to properly arrange the target structure in the radiation isocenter. The radiation source 1 may include a linear particle accelerator or another radiation source, such as a cobalt source, for producing an ionizing radiation beam. Further, the radiation source 1 is provided with a collimator 4 for shaping the radiation beam. The collimator 4 may particularly allow for varying the radiation intensity across the radiation beam in a defined way. For this purpose, the collimator 4 may be configured as a multi-leaf collimator (MLC), which comprises leafs that can independently be moved into and out of the radiation beam to form the cross section of the beam.

During delivery of the radiation therapy treatment, radiation is delivered to the target structure under varying beam directions and the intensity of the radiation emitted by the radiation source 1 may be varied. Moreover, the configuration of the collimator 4 may be changed based on the treatment plan so that the radiation beam is delivered with a time-varying shape. The related treatment parameters including the beam directions and intensities and the collimator configurations are defined in a treatment plan.

In one implementation, the radiation therapy treatment is delivered in accordance with successive segments, where each segment corresponds to one configuration of the treatment parameters defined in the treatment plan. In between two segments, the configuration is changed from the configuration of the first of the segments to the configuration of the second of the segments. During this period, the radiation beam may be turned off—this is usually referred to as step-and-shoot approach. Likewise, it is possible to continuously change the configuration in accordance with the segments without interrupting the radiation beam. This approach is applied in so-called volume modulated arc therapy (VMAT), for example.

For controlling the components of the radiation therapy treatment system, including the radiation source 1, the collimator 4, the gantry 3 and the patient support during the treatment, the treatment system includes a control unit 5. Preferably, the control unit 5 is implemented as a software program which comprises the control routines carried out by the control units and which is executed in a computer device coupled to the further components of the radiation therapy treatment system.

The treatment plan may be generated in a planning unit 6 prior to the treatment on the basis of an image of the region of interest of the patient body including the target structure and the surrounding OARs, which is also referred to as planning image herein. The planning image may be acquired using an imaging device 7 configured in accordance with a suitable imaging modality, which may be included in the system. If the system includes such an imaging device 7 as shown in FIG. 1, it may also be possible to adapt the treatment plan during the course of the treatment on the basis of images acquired during the treatment in a way known to a person skilled in the art. As an alternative, the planning image may also be acquired using an imaging device external to the system.

The planning unit 6 may be configured as a computer device, such as, for example a personal computer, comprising a processing unit which executes a treatment planning software for generating treatment plans for controlling the execution of the radiation therapy treatment. Further, the planning unit 6 comprises a suitable interface for receiving a planning image acquired as explained above. Moreover, the planning unit 6 comprises or is coupled to a user interface for interacting with a user (which may e.g. be a physician). The user interface may particularly comprise a display unit 8 and an input device 9. The input device 9 may particularly allow for navigating within a graphical user interface provided on the display unit 8. For this purpose, the input device 9 may particularly comprise a pointing device, such as, for example, a computer mouse, a track pad or a trackball. Likewise, the display unit 8 may comprise a touch-sensitive monitor which also serves as input device 9.

In the planning unit 6, the treatment plan for the radiation therapy treatment of a particular patient is generated on the basis of the planning image and on the basis of a clinical prescription for the patient, which may particularly specify treatment goals with respect to the target structure. The treatment goals may include the delivery of a certain minimum radiation dose to the target structure during the treatment. In addition, treatment goals with respect to the OARs may be specified. These treatment goals may include the delivery of maximum radiation doses to be delivered to the OARs. On the basis of the treatment goals, the planning unit 6 generates the treatment plan to achieve an optimized radiation dose distribution during the treatment such that the treatment goals are fulfilled. In order to generate the treatment plan in such a way, the planning unit 6 carries out an optimization procedure to determine optimized values of relevant treatment parameters.

In the optimization procedure, a cost function, which depends on the treatment parameters, may be set up on the basis of the treatment goals in a way known to the person skilled in the art and minimized with respect to the treatment parameters. This may be done using an automatic minimization algorithm and/or in a user-guided iterative optimization procedure comprising several steps. In each step of this procedure, the planning unit 6 automatically calculates a preliminary treatment plan by approximating a solution of the optimization problem. Then, the planning unit 6 determines the dose distribution corresponding to this treatment plan and visualizes the dose distribution to the user of the planning unit 6. The user then reviews the dose distribution to decide whether he/she is satisfied with the dose distribution. If this is the case in one step, the treatment plan calculated in this step is used as the pre-optimized treatment plan. If the user is not satisfied, the optimization problem is modified in accordance with changes specified by the user as a result of his/her review. Then, the planning unit 6 calculates a new preliminary treatment plan in the next step and the procedure continues until an acceptable dose distribution is achieved.

In the planning process, the planning unit 6 determines the dose distribution corresponding to the treatment plan on the basis of an estimate calculated using a model of the treatment delivery system, which particularly models the radiation source 1 and the collimator 4. However, particularly due to inaccuracies of the model this estimate does usually not exactly correspond to the actual dose distribution which is delivered to the patient when the calculated treatment plan is executed by means of the treatment delivery system.

Moreover, in case of a VMAT treatment, the radiation is continuously delivered with varying collimator configurations while the radiation source 1 moves along an optimized arc. In the planning unit 6, this arc is only determined on the basis of a number of discretized positions thereof. Thus, the arc is determined on the basis of an approximation (which is also referred to as small arc approximation) that results in inaccuracies or errors of the delivered dose distribution compared with the planned dose distribution, where the sizes of the errors particularly depend on the number of discretized positions considered in the planning procedure. The number of discretized positions used in the planning process is usually a compromise between accuracy, which can be increased by increasing the number of positions, and the computation time for determining the treatment plan, which likewise increases with the number of positions. Therefore, there is often a non-negligible deviation between the planned dose distribution and the delivered dose distribution.

In order to ensure that the treatment goals can be fulfilled despite the aforementioned deviations between the planned dose distribution and the delivered dose distribution, each treatment plan usually undergoes a QA test before a treatment is delivered to the patient on the basis of the treatment plan, and the treatment plan is only used for controlling the treatment of the patient upon approval thereof in the QA test.

In the QA test, the treatment plan is executed while a phantom is positioned in the treatment zone 2, which comprises one or more dosimeters for measuring the radiation dose distribution corresponding to the treatment plan. Then, the measured dose distribution may be compared with the optimized dose distribution corresponding to the treatment plan as determined in the planning unit 6, which is also referred to as planned dose distribution herein. In this comparison, the deviations between the measured and the planned distribution are determined. Then, it is judged automatically or by the operator of the planning unit 6, whether or not the deviations are acceptable. If yes, the successfully tested treatment plan is used for the subsequent treatment of the patient. If not, the treatment plan is not used in the treatment, but a new treatment plan is generated for the patient.

In order to assess the deviations between the planned dose distribution and measured dose distribution, suitable deviation parameters are determined and evaluated using associated threshold values. In this evaluation, a treatment plan may be regarded as being acceptable and may pass the QA test, if the fraction of positions with deviation parameters not being compliant with the threshold value exceeds a predetermined value and/or if the values of the deviation parameters for all positions of the region of interest are within predetermined limits.

In specific embodiments, the deviation parameters may correspond to the dose differences at each point of the region of interest or the distance-to-agreement (DTA) values at each point of the region of interest. Given a particular position of the region of interest, the associated DTA value is the distance to the nearest point where the measured dose value corresponds to the planned dose value according to the planned dose distribution.

Moreover, in a preferred embodiment, so called gamma indices are determined as deviation parameters for each point of the region of interest. The gamma index is determined by a combined calculation of the difference between the planned dose value and the measured dose value at a particular point and a DTA value for the point. In particular, the gamma index may be calculated on the basis of a gamma function $$\Gamma(\vec{r}_e, \vec{r}_r) = \sqrt{\frac{r^2(\vec{r}_e, \vec{r}_r)}{\Delta d^2} + \frac{\delta^2(\vec{r}_e, \vec{r}_r)}{\Delta D^2}}$$

where $r(\vec{r}_e, \vec{r}_r)$ is the distance between a point $\vec{r}_e$ of the measured dose distribution and a point $\vec{r}_r$ of the planned dose distribution, $\delta(\vec{r}_e, \vec{r}_r)$ is the difference between the planned dose value at the point $\vec{r}_e$ and the measured dose values at the point $\vec{r}_r$, $\Delta d$ is a DTA criterion and $\Delta D$ is a dose difference criterion. The DTA criterion and the dose difference criterion have predetermined values. For instance, the dose difference criterion may be selected to be 3% of the maximum dose and the DTA criterion may be selected to be 3 mm. On the basis of the gamma function, the gamma index $\gamma$ for the position $\vec{r}_r$ of the planned dose distribution may be calculated as the minimum of the gamma function with respect to all points $\vec{r}_e$:

$$\gamma(\vec{r}_r) = \min\{\Gamma(\vec{r}_e, \vec{r}_r)\} \forall \{\vec{r}_e\}.$$

One exemplary algorithm for calculating the gamma indices, which may be applied in the planning unit 6, is described in the publication M. Wendling et al., "A fast algorithm for gamma evaluation in 3D", Med. Phys. 34(5): 1647-54, 2007.

In the assessment of the treatment plan with respect to a particular position, a value of the related gamma index which is equal to or smaller than 1 may be regarded as acceptable. The complete treatment plan may be assessed by evaluating the gamma indices for all positions of the planned dose distribution in the region of interest including the target structure and the surrounding OAERs. This evaluation may be carried out on the basis of a gamma histogram, for example. In this evaluation, the treatment plan may be regarded as being acceptable and passed to the QA test, if the fraction of positions having unacceptable gamma indices (i.e. gamma indices greater than one) is smaller than a pre-determined threshold value, which may be 5%, for example Moreover, the distribution of gamma indices and/or related statistical quantities (e.g. the minimum, the maximum and the mean value together with the related standard deviation) may be presented to the user of the planning unit 6 at the display unit 8, and the user may inspect the distribution of the gamma indices and/or the statistical quantities in order to determine whether the treatment plan can be regarded as being acceptable. This manual evaluation may be made in addition to evaluation of the fraction of positions having unacceptable gamma indices.

As the QA tests of the treatment plans are quite time-consuming and expensive due to the required measurement of the dose distribution using the phantom and given that each QA test blocks a treatment delivery apparatus, each optimized treatment plan is preferably already evaluated prior to the QA test. In this evaluation, it is assessed whether or not the treatment plan will likely pass the QA test. If it is determined that this is the case, the QA test is actually carried out for the treatment plan. However, if it is determined that the treatment plan will likely not pass the QA test, the treatment plan will be discarded and a new treatment plan may be generated for the respective patient. Hereby, QA tests that are likely to fail can be avoided and, thus, the complete planning process including the QA testing can be performed more efficiently.

In order to carry out this evaluation for a treatment plan, an evaluation unit 10 of the planning unit 6 determines values of each of a plurality of treatment plan metrics. These values may then be compared with threshold values in order to assess whether or not the treatment plan will likely pass the QA test. This comparison may be made automatically and/or manually by the user of the planning unit 6. In order to enable the manual comparison, the planning unit 6 may provide a graphical user interface comprising a scoreboard as will be explained further explained herein below.

The evaluation unit 10 is configured to calculate values of a plurality of different treatment plan metrics, which are stored in the evaluation unit 10. In specific embodiments, the evaluation unit 10 may be programmed to calculate values of 2-10 different treatment plan metrics. However, it is also possible that values of more than 10 treatment plan metrics are calculated in the evaluation unit 10. The treatment plan metrics stored in the evaluation unit 10 may selected among any suitable metrics known in the art. In particular, the metrics may be calculated on the basis of one or more of the travel, the velocity and the acceleration of the MLC leaves during the treatment and/or on the basis of quantities parameterizing a complexity of the MLC configurations specified in the treatment plan, such as, for example, the ratio between the perimeters and the open areas of the MLC apertures or a quantity indicative of changes among adjacent beamlets of the radiation beam.

Exemplary metrics include the average leaf travel as proposed in the above-mentioned publication by L. Masi et al. for the evaluation of VMAT treatment plans. In order to determine the average leaf travel, the entire travel over the VMAT arc is calculated for each MLC leaf and, then, the determined values are averaged (where leaves that remain closed during the treatment are not considered in the evaluation). As shown in the publication, there is a negative correlation between this average leave travel and unacceptable gamma indices such that there is an in increased likelihood that treatment plans with an average leaf travel above a certain threshold do not pass the QA test.

A further exemplary metric, which may be used for the evaluation of VMAT treatment plans, is in an MLC-based complexity metric as discussed in the above-mentioned publication by K. C. Younge et al. This metric is related to the complexity of the treatment plan with respect to its execution in the treatment delivery system and is calculated on the basis of the sum over all apertures of the MLC during a treatment of the product of the number of monitor units (MUs) delivered through the respective aperture and the ratio between the aperture perimeter and the open area of the respective aperture. It was found that treatment plans having a value of this metric which is larger than a threshold value have an increased likelihood to fail in the QA test.

Further metrics which may be evaluated in the evaluation unit 10 in order to evaluate VMAT treatment plans include the maximum MLC leaf speed and acceleration. As shown in the publication J. M. Park et al. "The effect of MLC speed and acceleration on the plan delivery accuracy of VMAT", Br J Radiol 2015; 88:20140698, treatment plans resulting in maximum MLC leaf speeds and/or accelerations above related thresholds, have an increased likelihood to fail in the QA test.

A further exemplary metric, which may be applied in order to evaluate treatment plans for the treatment delivery on the basis of the step-and-shoot approach, is the modulation index discussed in the publication G. Nicolini et al., "What is an acceptably smoothed fluence? Dosimetric and delivery considerations for dynamic sliding window IMRT", Radiation Oncology 2007, 2:42. This index is a measure of the complexity of the MLC configurations and is calculated on the basis of the fraction of changes among adjacent beamlets of the radiation beam that exceeds a certain value. The index may be compared with an upper threshold as values of the index which are greater than such a threshold can be indicative of an increased likelihood that a treatment plan does not pass the QA test.

As a last example of a possible treatment plan metric than can be calculated in the evaluation unit 10, reference is made to the small aperture score described in the publication S. B. Crowe et al., "Treatment plan complexity metrics for predicting IMRT pre-treatment quality assurance results", Australas Phys Eng Sci Med (2014) 37:475-482. The small aperture score is calculated as the ratio of open leaf pairs, where the aperture is less than a defined threshold, to all open leaf pairs. As shown in this publication, the value of this metric may be compared with an upper threshold value as treatment plans with a large aperture score have an increased likelihood of failing in the QA test.

In the evaluation unit 10, a number of suitable treatment plan metrics are stored which are applicable for the evaluation of the types of treatment plans (i.e. for VMAT or step-and-shoot) generated in the planning unit 6. In case treatment plans of several types are generated in the planning unit 6 (which is usually the case), the evaluation unit 10 may select the metrics applicable to each individual treatment plan to be evaluated on the basis of the type of this treatment plan.

For the treatment plan metrics stored in the evaluation unit 10, the evaluation unit 10 may determine threshold values on the basis of which treatment plans which will likely pass the QA test can be distinguished from treatment plans which will likely not pass the QA test. The threshold values are determined such that a treatment plan having a value of a metric which is not compliant with the threshold value, i.e. which is smaller than a lower threshold value or larger than an upper threshold value, will likely not pass the QA test. Upon having determined the threshold values—or upon having updated the threshold values as will be explained further below—the threshold values are stored in order to be used in the assessment of new treatment plans.

In order to determine the threshold values, the evaluation unit 10 accesses a database 11 storing historic treatment plans, which have undergone a QA test in the system. In the database 11, historic treatment plans may particularly be stored which have undergone a QA test in the treatment delivery system for which the treatment plan to be evaluated is generated so that the specific characteristics of this system are taken into consideration. However, the database 11 may also store treatment plans which have undergone QA tests in other systems.

For each of the treatment plans, a quality indicator is stored which indicates the result of the QA test (i.e. passed or failed) of the treatment plan. In addition or as an alternative, the database 11 may store the gamma index each the treatment plan as determined during the QA test of the respective treatment plan. As explained above, both the quality indicator and the gamma indices correspond to quality parameters indicating whether the deviations between the planned dose distribution corresponding to the treatment plan and the measured dose distribution are within acceptable limits.

Using the stored quality parameters, the evaluation unit 10 may determine a threshold value for a particular metric by calculating values of the metric for all historical treatment plans stored in the database 11. Then, the evaluation unit 10 may perform a correlation analysis between the values of the metric and the quality parameters in order to distinguish values of the metric that are indicative of treatment plans which likely pass the QA test from values of the metric that are indicative of treatment plans which likely do not pass the QA test. For instance, the evaluation unit 10 may determine the correlation between the values of a specific metric and the results of QA tests (i.e. the quality indicators) for the treatment plans stored in the database 11. In addition or as an alternative, the evaluation unit 10 may determine the correlation between the values of the metric and acceptable values of the gamma index for the treatment plans stored in the database 11. On the basis of such correlations, the evaluation unit 10 may determine the threshold values for the respective metric such that values compliant with the threshold value are indicative of treatment plans that will likely pass the QA test.

In addition, the evaluation unit 10 may carry out a receiver operator characteristics (ROC) analysis on the basis of the quality indictors specifying the results of the QA tests of the treatment plans stored in the database 11. The ROC analysis, which is known to the person skilled in the art as such, particularly allows for determining the performance of binary classifiers. In the evaluation unit 10, the ROC analysis may be applied in order to optimize the threshold values associated with the treatment plan metrics (which effectively define a binary classifier for distinguishing between treatment plans that will likely pass the QA test from treatment plans that will likely not pass the QA test).

Since the threshold values for evaluating the treatment plan metrics are determined on the basis of historic treatment plans generated for the same treatment delivery system as the treatment plan to be assessed in the evaluation unit 10, the threshold values can generally be selected on the basis of the statistical evaluation such that a reliable prediction of the outcome of QA tests in the treatment delivery system is possible.

Moreover, each treatment plan for which a new QA test is performed in the treatment delivery system may be stored in the database 11 along with the related quality parameters. Thus, the database 11 is updated each time a new QA test is performed in the system so that the data basis for determining the threshold values for evaluating the treatment plan metrics continuously grows. In order to make use of this growing data basis, the evaluation unit 10 may optimize the threshold values on a regular basis. In each optimization step, the evaluation unit 10 may particularly adapt the threshold values associated with the treatment plan metrics to the new treatment plans which have been stored in the database 11 since the previous optimization step. Thus, the threshold values can be optimized on a continuing basis.

Furthermore, it is preferably also possible for the users of the evaluation unit 10 to manually specify threshold values such that these values are used in the treatment plan evaluation instead of automatically generated threshold values. A manual specification of a threshold values for a certain metric may be provided instead of the automatic determination. Likewise, a threshold value may be specified manually for a certain treatment plan metric upon a previous automatic determination thereof, e.g. in order to replace the automatically generated threshold value in case the user considers this value to be inappropriate. In such a way, the user of the evaluation unit 10 can particularly specify threshold values for one or more treatment plan metrics, which overrule the automatically generated threshold values. Moreover, it is possible for the user to manually specify threshold values for one or more treatment plan metrics for which no automatic determination is carried out.

The option to specify threshold values manually may particularly be used in case the database 11 does not include a sufficiently large number of historic treatment plans and related quality indicators to determine a reliable threshold value on the basis of a statistical evaluation as explained above.

In addition to the threshold values, a flexibility threshold may be provided and stored in the evaluation unit 10 for each treatment plan metric and the related threshold value. A flexibility threshold for a particular threshold defines a value range in which a value of a metric that does not comply with the threshold value is regarded as partly compliant with the threshold value and may be considered to be acceptable—at least under certain circumstance (e.g. if the values of all or most of the other treatment plan metrics are compliant with the related threshold values). For the treatment plan metrics stored in the evaluation unit 10, such flexibility thresholds may be set by the user of the evaluation unit 10 on the basis of his expert knowledge and past experience.

When a new treatment plan is generated in the planning unit 6, it is evaluated in the evaluation unit 10 before it is passed to the QA test. In the evaluation unit 10, the values of the treatment plan metrics stored in the evaluation unit 10 are calculated. Moreover, the evaluation unit 10 may compare the calculated values of the treatment plan metrics with the related threshold values. Further, if a calculated value of a treatment plan does not comply with the related threshold value, the evaluation unit 10 may determine if the calculated value complies with the flexibility threshold so that it is to be regarded as being partly compliant with threshold value.

In one embodiment, the results of the aforementioned assessment of the treatment in the evaluation unit 10 are presented to the user of the planning unit 6 in a graphical user interface in order to allow the user to review the calculated values. In the graphical user interface, the calculated values of the treatment plan metric may be indicated. In addition, the threshold values and the flexibility thresholds may be indicated. For this purpose, the graphical user interface may comprise a table or scoreboard as schematically and exemplarily indicated in FIG. 2. In this scoreboard, calculated values 21*a*-21*d* of four treatment plan metrics A-D are indicated along with their related threshold values 22*a*-22*d* and their related flexibility thresholds 23*a*-23*d*.

Figure 2:
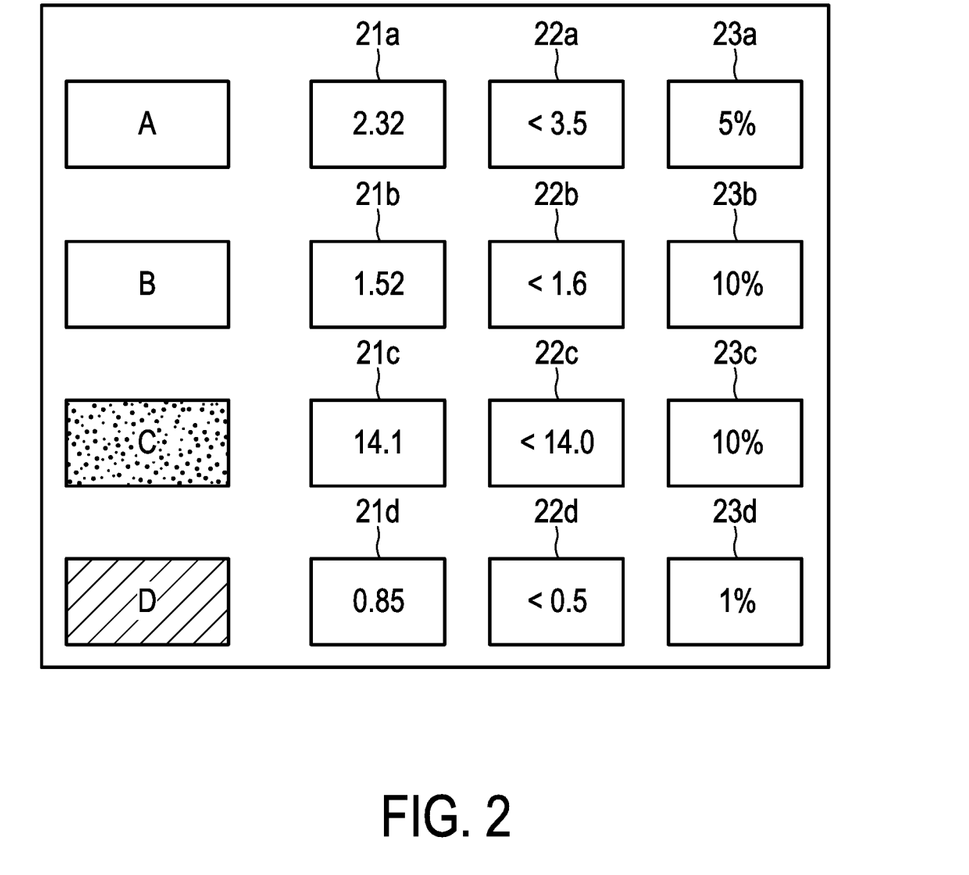

By inspecting the values provided in the graphical user interface, the user of the planning unit 6 may manually assess the treatment plan in order to approve the treatment for a subsequent QA test or in order to discard the treatment plan. In so doing, the user may approve a treatment plan if all calculated values of the treatment plan metrics are compliant with their related threshold values. Moreover, a treatment plan may also be approved in case only some calculated values are not compliant with the associated thresholds but are compliant with the associated flexibility thresholds. Furthermore, it may even be possible that a treatment plan is approved in case one or a greater subset of the calculated values does also not comply with the flexibility thresholds. The corresponding assessment of the treatment plan may be made by the user of the planning unit 6 on the basis of his knowledge about the treatment delivery system and his experience in planning radiation therapy treatments.

In order to assist the user in the manual evaluation of the treatment plan, the evaluation unit 10 may highlight the calculated values of the treatment plan metrics based on their compliance with the associated threshold values and flexibility thresholds. For instance, the calculated values may be highlighted using colors, particularly the colors of a traffic light. Thus, calculated values which do not comply with their associated threshold value and the related flexibility threshold may be highlighted using a first predetermined color (illustrated by hatched fields in FIG. 2), particularly red, and calculated values which do not comply with their associated threshold value but with the related flexibility threshold may be highlighted using a second predetermined color (illustrated by dotted fields in FIG. 2), particularly yellow. In addition, calculated values which are fully compliant with their associated threshold value may be highlighted using a third predetermined color, particularly green. On this basis of this highlighting, the user of the planning unit 6 can quickly determine the compliance of the calculated values with the related thresholds in order to validate the treatment plan as described above on the basis of this determination.

In addition, the evaluation unit 10 may control the display unit 8 to output an alarm notification if one or more calculated threshold values are not compliant with their associated threshold values. Hereby, an additional notification can be provided to the user in case a treatment plan can potentially not be approved due to the non-compliance of one or more calculate values of the treatment plan metrics with their associated threshold values. The notification may particularly indicate the relevant treatment plan metrics for which such a value has been calculated.

In one implementation, the approval of the user of the planning unit 6 is necessary for the treatment plan to be advanced to the QA test. This implementation is particularly useful in case the threshold values are not considered to be entirely reliable. This may particularly the case if the database 11 only contains a limited data basis for the determination of the threshold values so that the thresholds values can only be determined with limited confidence.

In a further implementation, the evaluation unit 10 only requests the user to manually validate the treatment plan in case one or more calculated values of the treatment plan metrics are not compliant with the associated threshold values. However, in case all calculated values comply with their related threshold values, the evaluation unit 10 may automatically approve the treatment so that it may be advanced to the QA test without an interaction with the user of the planning unit 6. Hereby, treatment plans can be validated more quickly.

In the way described above, treatment plans can be evaluated on the basis of treatment plan metrics in order to determine whether or they will likely pass the QA test so that only those treatment plans are advanced to the QA test for which this is case. In order to carry out this evaluation, the evaluation unit 10 may calculate values for all applicable treatment plan metrics which are stored therein. Alternatively, the user of the planning unit 6 may manually select the treatment plan metrics which are evaluated for a particular treatment plan to be validated from the set of available metrics.

Moreover, it may be possible for the user to manually specify and/or adapt the relevant parameters for evaluating a treatment plan, including a manual specification of threshold values as described above and/or a specification of the flexibility thresholds.

Figure 3:
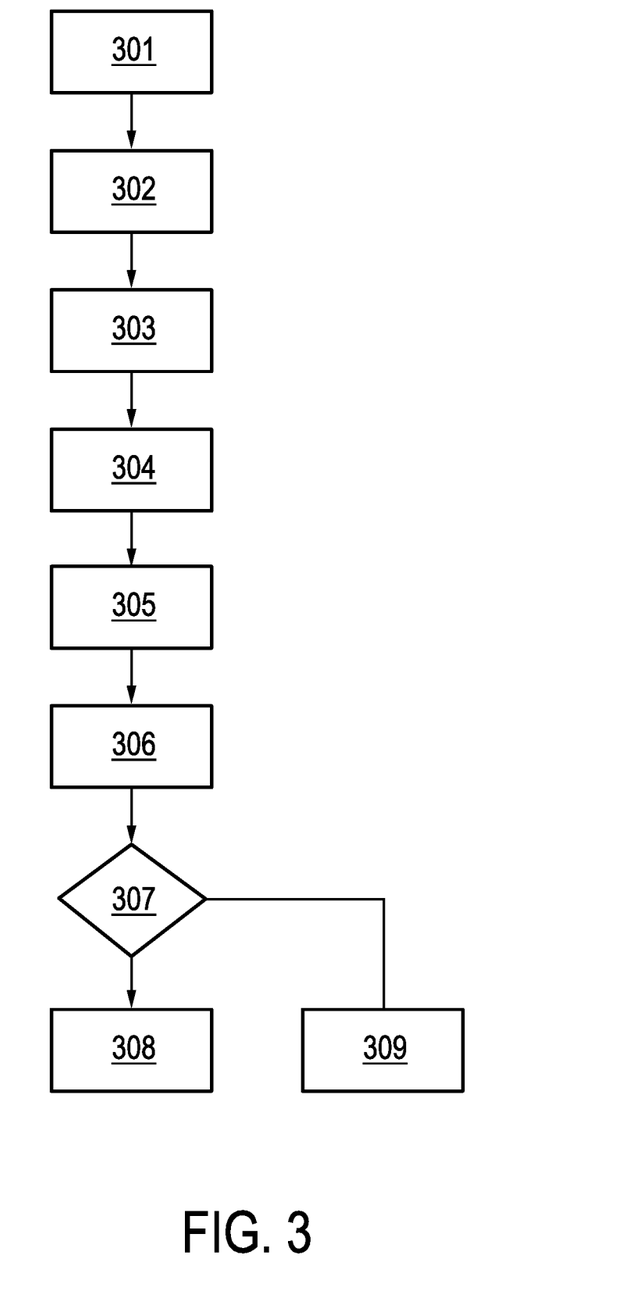

FIG. 3 schematically and exemplarily shows steps of one embodiment of method for evaluating a treatment plan in the system described above:

In order to prepare the evaluation, historic treatment plans may be stored in the database 11 together with related quality indicators as explained above (step 301). On the basis of the historic treatment plans and the associated quality indicators, the evaluation unit 10 may then determine threshold values for each of the treatment plan metrics stored in the evaluation unit 10 in step 302 on the basis of a statistical evaluation of the historic treatment plans and the related quality indicators. In addition, flexibility thresholds may be provided for the treatment plan metrics in step 303. Moreover, the user of the planning unit 6 may manually specify threshold values which take precedence over the automatically generated threshold values as described above and/or the user may manually specify threshold values for treatment plan metrics for which no automatic generation of the threshold values is carried out by the evaluation unit 10.

In order to evaluate a specific treatment plan generated in the planning unit 6, the evaluation unit 10 may calculate a value for each of the treatment plan metrics which are stored in the evaluation unit 10 and which are applicable to the specific treatment plan (step 304). The calculated values are then compared to the threshold values and to the related flexibility thresholds, if such flexibility thresholds are available (step 305). Moreover, the calculated values and the result of the comparisons may be provided for a validation of the treatment plan in step 306.

As explained above, the validation may be exclusively carried out by the user of the planning unit 6 in one embodiment. For this purpose, the calculated values of the treatment plan metrics and the results of the comparison may be provided in the graphical user interface, particularly in the form a scoreboard as exemplarily and schematically shown in FIG. 2. The user may then inspect the values in order to assess whether the treatment plan is passed to the QA test or whether a re-optimization of the treatment plan is to be carried out.

In the alternative embodiment shown in FIG. 3, a semi-automatic evaluation of the treatment plan is carried out. In this embodiment, the evaluation unit 10 checks in step 307 whether all calculated values of the treatment plan metrics are compliant with the related threshold values. If this is the case, the treatment plan is automatically passed to the QA test in step 308. If the evaluation unit 10 determines in step 307 that one or more calculated values are not compliant with the related threshold values, the calculated values and the results of the comparison of these values with the associated threshold values and flexibility thresholds may be presented to the user for a manual validation of the treatment plan as in the aforementioned embodiment.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for evaluating a treatment plan for an external radiation therapy treatment of a patient delivered using an external beam radiation therapy apparatus, the treatment plan comprising parameters for controlling the external beam radiation therapy apparatus during the treatment, the system comprising:
a database storing a plurality of historic treatment plans and storing for each historic treatment plan a quality parameter indicative of whether a deviation between a planned dose distribution corresponding to the respective treatment plan and a measured dose distribution resulting from an execution of the treatment plan is within an acceptable limit; and
an evaluation unit configured to: determine a threshold value for each of a plurality of treatment plan metrics on a basis of the historic treatment plans and associated quality parameters; calculate a value of each of the plurality of treatment plan metrics for the treatment plan and to compare the value of each of the plurality of treatment plan metrics with the threshold value determined for the respective metric and to provide the result of the calculation and/or the comparison for a validation of the treatment plan; and compare the calculated value of each of the plurality of treatment plan metrics with an associated further flexibility threshold, wherein the value of the flexibility threshold does not comply with the threshold values determined for the metric.

2. The system as defined in claim 1, wherein the evaluation unit is configured to determine the threshold values for the treatment plan metrics on the basis of a statistical analysis of the quality parameters associated with the treatment plans stored in the database.

3. The system as defined in claim 1, wherein the quality parameter associated with a treatment plan comprises an indication of a result of a quality assurance test of the treatment plan and/or gamma indices determined for the treatment plan.

4. The system as defined in claim 1, wherein the database can be updated to store further treatment plans and associated quality parameters and wherein the evaluation unit is configured to adapt the determined threshold values to the further treatment plans upon an update of the database.

5. The system as defined in claim 1, wherein the evaluation unit is configured to receive a threshold value input by a user of the system for at least one of the treatment plan metrics and to compare the calculated value for the respective treatment plan metric with said threshold value instead of the threshold value determined on the basis of the historic treatment plans and the associated quality parameters.

6. The system as defined in claim 1, wherein the evaluation unit is configured to receive a threshold value input by a user of the system for at least one further treatment plan metric, to calculate a value of the further metric for the treatment plan and to compare the calculated value with said threshold value and/or to provide the result of the calculation and/or the comparison for a validation of the treatment plan.

7. The system as defined in claim 1, wherein the evaluation unit is configured to present the calculated values of the metrics to a user of the system in a graphical user interface in order to allow for a validation of the treatment plan by the user.

8. The system as defined in claim 1, wherein the evaluation unit is configured to highlight the calculated values in a graphical user interface based on their compliance with the threshold value determined for the respective metric and/or with the associated flexibility threshold.

9. The system as defined in claim 1, wherein the evaluation unit is configured to present the calculated values of the metrics in a graphical user interface only in case the calculated value of at least one of the metrics is not compliant with its associated threshold value.

10. The system as defined in claim 9, wherein the evaluation unit is configured to automatically accept the treatment plan if the calculated values of all metrics are compliant with their associated thresholds.

11. The system as defined in claim 1, wherein the system is configured to carry out a quality assurance test for the treatment plan if the treatment is accepted as the result of its validation.

12. The system as defined in claim 1, wherein the external beam radiation therapy apparatus comprises a radiation source for generating a radiation beam to be delivered to the patient and a collimator for forming the radiation beam, the treatment plan comprising parameters for controlling the radiation source and/or the collimator during the treatment.

13. A method for evaluating a treatment plan for an external radiation therapy treatment of a patient delivered using an external beam radiation therapy apparatus, the treatment plan comprising parameters for controlling the external beam radiation therapy apparatus during the treatment, the method comprising:
  storing a plurality of historic treatment plans in a database and storing for each historic treatment plan a quality parameter indicative of whether a deviation between a planned dose distribution corresponding to the respective treatment plan and a measured dose distribution resulting from an execution of the treatment plan is within an acceptable limit;
  determining a threshold value for each of a plurality of treatment plan metrics on a basis of the historic treatment plans and associated quality parameters;
  calculating a value of each of the plurality of treatment plan metrics for the treatment plan;
  comparing the value of each of the plurality of treatment plan metrics with the threshold value determined for the respective metric;
  providing the result of the calculation and/or the comparison for a validation of the treatment plan; and
  comparing the calculated value of each the plurality of treatment plan metrics with an associated further flexibility threshold, where the value of the flexibility threshold does not comply with the threshold values determined for the metric.

14. The method as defined in claim 13, further comprising:
  determining the threshold values for the treatment plan metrics on the basis of a statistical analysis of the quality parameters associated with the treatment plans stored in the database.

15. The method as defined in claim 13, wherein the quality parameter associated with a treatment plan comprises an indication of a result of a quality assurance test of the treatment plan and/or gamma indices determined for the treatment plan.

16. The method as defined in claim 13, further comprising:
  updating the database to store further treatment plans and associated quality parameters, wherein an evaluation unit is configured to adapt the determined threshold values to the further treatment plans upon an update of the database.

17. A tangible, non-transitory computer readable medium that stores instructions, which when executed by a processor, cause the processor to:
  store a plurality of historic treatment plans in a database and store for each historic treatment plan a quality parameter indicative of whether a deviation between a planned dose distribution corresponding to the respective treatment plan and a measured dose distribution resulting from an execution of the treatment plan is within an acceptable limit;
  determine a threshold value for each of a plurality of treatment plan metrics on a basis of the historic treatment plans and associated quality parameters;
  calculate a value of each of the metrics for the treatment plan;
  compare the value of each of the metrics with the threshold value determined for the respective metric;
  provide the result of the calculation and/or the comparison for a validation of the treatment plan; and
  compare the calculated value of each the metrics with an associated further flexibility threshold, where the value of the flexibility threshold does not comply with the threshold values determined for the metric.

18. The tangible, non-transitory computer readable medium of claim 17, wherein the instructions, when executed by the processor, further cause the processor to:
  determine the threshold values for the treatment plan metrics on the basis of a statistical analysis of the quality parameters associated with the treatment plans stored in the database.

19. The tangible, non-transitory computer readable medium of claim 17, wherein the quality parameters associated with a treatment plan comprises an indication of a result of a quality assurance test of the treatment plan and/or gamma indices determined for the treatment plan.

20. The tangible, non-transitory computer readable medium of claim 17, wherein the instructions, when executed by the processor, further cause the processor to:
  update the database to store further treatment plans and associated quality parameters, wherein an evaluation unit is configured to adapt the determined threshold values to the further treatment plans upon an update of the database.

* * * * *